United States Patent
Beidler et al.

(10) Patent No.: US 9,290,570 B2
(45) Date of Patent: Mar. 22, 2016

(54) PAN-ELR+ CXC CHEMOKINE ANTIBODIES

(71) Applicant: Eli Lilly and Company, Indianapolis, IN (US)

(72) Inventors: Catherine Brautigam Beidler, Poway, CA (US); Kristine Kay Kikly, Spiceland, IN (US); Beth Ann Strifler, Brownsburg, IN (US); Derrick Ryan Witcher, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 44 days.

(21) Appl. No.: 14/204,089

(22) Filed: Mar. 11, 2014

(65) Prior Publication Data

US 2014/0271647 A1    Sep. 18, 2014

Related U.S. Application Data

(60) Provisional application No. 61/793,615, filed on Mar. 15, 2013.

(51) Int. Cl.
```
A61K 39/00    (2006.01)
A61K 39/395   (2006.01)
C07K 16/00    (2006.01)
C07K 16/18    (2006.01)
C07K 16/22    (2006.01)
C07K 16/24    (2006.01)
```

(52) U.S. Cl.
CPC ............ C07K 16/244 (2013.01); A61K 39/3955 (2013.01); C07K 16/24 (2013.01); *A61K 2039/505* (2013.01); *A61K 2039/545* (2013.01); *C07K 2317/34* (2013.01); *C07K 2317/76* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

WO    2008130969    10/2008

OTHER PUBLICATIONS

Yang, X., et al., "Fully Human Anti-Interleukin-8 Monoclonal Antibodies: Potential Therapeutics for the Treatment of Inflammatory Disease States," J Leuk Biol 66, pp. 401-410 (1999).

Skov, L, et al., "IL-8 Antibody Therapeutic Target in Inflammatory Diseases: Reduction of Clinical Activity in Palmoplantar Pustulosis," J Immunol 181, pp. 669-679 (2008).

*Primary Examiner* — Elizabeth C Kemmerer
(74) *Attorney, Agent, or Firm* — Duane C. Marks

(57) ABSTRACT

Antibodies are provided that specifically bind seven human ELR+ CXC chemokines. The antibodies of the invention are useful for treating various inflammatory/autoimmune diseases, such as inflammatory bowel disease (IBD), plaque psoriasis, and palmoplantar pustulosis; and cancer, such as renal cancer or ovarian cancer.

12 Claims, No Drawings

PAN-ELR+ CXC CHEMOKINE ANTIBODIES

The present invention relates to antibodies against ELR+ CXC chemokines, and their use in treating diseases where pathogenesis is mediated by ELR+ CXC chemokines.

ELR+ CXC chemokines (so-called because members of the chemokine family all possess an E-L-R amino acid motif immediately adjacent to their CXC motif) play an important role in a variety of pathogenic mechanisms, including the migration of neutrophils to sites of inflammation and angiogenesis. Neutrophils contribute to the pathogenesis of several acute and chronic inflammatory/autoimmune diseases, such as inflammatory bowel disease (IBD), plaque psoriasis, and palmoplantar pustulosis. ELR+ CXC chemokines also play a critical role in tumorigenesis and tumor metastasis. These chemokines are highly expressed in tumors. Within the tumor environment, ELR+ CXC chemokines are involved in various pathways, for example angiogenesis, mobilization and invasion of endothelial cells and leukocytes at tumor sites, and proliferation and survival of tumor cells.

Chemokines are grouped into four subfamilies: CXC, CC, (X)C, and CX3C. In the CXC chemokines, one amino acid separates the first two cysteines ("the CXC motif"). ELR+ CXC chemokines are ligands for CXCR1 and/or CXCR2 chemokine receptors, which are G-protein coupled seven transmembrane domain-type receptors that specifically bind ELR+ CXC chemokines. The seven human ELR+ CXC chemokines are human Gro-alpha (also known as CXCL1), human Gro-beta (also known as CXCL2), human Gro-gamma (also known as CXCL3), human ENA-78 (also known as CXCL5), human GCP-2 (also known as CXCL6), human NAP-2 (also known as CXCL7), and human IL-8 (also known as CXCL8). All ELR+ CXC chemokines bind the CXCR2 receptor; moreover, some ELR+ CXC chemokines bind both CXCR1 and CXCR2 receptors (i.e., CXCL6 and CXCL8), all of which contributes to redundancy in the activation pathways.

Antibodies that bind to individual ELR+ CXC chemokines have been previously described. Two monoclonal antibodies against CXCL8 (IL-8) have been evaluated in early clinical trials with efficacy in inflammatory diseases. (J Leuk Biol 66:401-410; J Immunol 181:669-679.) In addition, WO 2008/130969 discloses an antibody that binds to human IL-8 (CXCL8), human Gro-alpha (CXCL1), human Gro-beta (CXCL2), human Gro-gamma (CXCL3), and human ENA-78 (CXCL5). However, the disclosure does not demonstrate that the antibody binds tightly to GCP-2 (CXCL6), and is silent regarding binding to NAP-2 (CXCL7).

However, an antibody that is able to bind and neutralize all seven human ELR+ CXC chemokines has not yet been disclosed. Targeting one or a few human ELR+ CXC chemokines leaves open the opportunity for other ELR+ CXC chemokines to elicit multiple biological functions. Neutralizing all seven ELR+ CXC chemokines could impact the ability of CXCR1+ or CXCR2+ cells to migrate to sites of inflammation and could inhibit angiogenesis. Given the significant redundancy in the CXCR1 and CXCR2 receptor activation pathways, there is still a need for an antibody that binds all seven human ELR+ CXC chemokines with specificity and with high affinity. There is a need for an antibody that neutralizes all seven human ELR+ CXC chemokines. There is also a need for an antibody that is physically stable. It is therefore desirable to provide a septa-specific antibody that is able to bind and neutralize all seven human ELR+ CXC chemokines, and is physically stable.

The present invention provides an antibody comprising a light chain and a heavy chain, wherein the light chain comprises a light chain variable region (LCVR) and the heavy chain comprises a heavy chain variable region (HCVR), wherein the LCVR comprises LCDR1, LCDR2, LCDR3 and the HCVR comprises HCDR1, HCDR2, HCDR3, wherein LCDR1 is RASQSISNNLH (SEQ ID NO: 7), LCDR2 is YTSRSVS (SEQ ID NO: 8), LCDR3 is GQNNEWPEV (SEQ ID NO: 9), HCDR1 is GYEFTSYWIH (SEQ ID NO: 10), HCDR2 is NISPNSGSANYNEKFKS (SEQ ID NO: 11), and HCDR3 is EGPYSYYPSRXaaYYGSDL (SEQ ID NO: 20) wherein Xaa is E or Q.

The present invention provides in another aspect an antibody wherein the amino acid sequence of the HCVR is SEQ ID NO: 2 or SEQ ID NO: 14. The present invention further provides an antibody wherein the amino acid sequence of the LCVR is SEQ ID NO: 4 or SEQ ID NO: 16.

The present invention provides an antibody wherein the amino acid sequence of the heavy chain is SEQ ID NO: 1 or 13. The present invention also provides an antibody wherein the amino acid sequence of the light chain is SEQ ID NO: 3 or 15.

The present invention also provides a DNA molecule comprising a first polynucleotide sequence encoding a polypeptide having the amino acid sequence of SEQ ID NO: 1 or 13; and comprising a second polynucleotide sequence encoding a polypeptide having the amino acid sequence of SEQ ID NO: 3 or 15.

The present invention provides a mammalian cell comprising the DNA molecules described above, wherein the cell is capable of expressing an antibody comprising a heavy chain having an amino acid sequence of SEQ ID NO: 1 or 13 and a light chain having an amino acid sequence of SEQ ID NO: 3 or 15. Mammalian host cells known to be capable of expressing functional immunoglobulins include Chinese Hamster Ovary (CHO) cells, COS cells, and NSO cells. Preferred host cells for use in the invention are NSO cells.

The present invention further provides a process for producing an antibody comprising a light chain whose amino acid sequence is SEQ ID NO: 3 or 15 and a heavy chain whose amino acid sequence is SEQ ID NO: 1 or 13, comprising cultivating a mammalian cell described above under conditions such that the antibody is expressed, and recovering the expressed antibody.

The present invention provides a method of treating ulcerative colitis, renal cancer, or ovarian cancer, comprising administering to a patient in need thereof a therapeutically effective amount of an antibody of the present invention.

The present invention further provides an antibody of the present invention for use in therapy. Furthermore, the present invention provides an antibody of the present invention for use in the treatment of ulcerative colitis, renal cancer, or ovarian cancer. Additionally, the present invention provides the use of an antibody of the present invention in the manufacture of a medicament for the treatment of ulcerative colitis, renal cancer, or ovarian cancer.

The present invention provides a pharmaceutical composition comprising an antibody of the present invention and one or more pharmaceutically acceptable carriers, diluents, or excipients.

As used herein, the term "human ELR+ CXC chemokines" is intended to refer to the seven known CXC chemokines that have an E-L-R motif and that bind to CXCR1 and/or CXCR2 receptor. The human ELR+ CXC chemokines are human Gro-alpha (also known as CXCL1) (SEQ ID NO: 21), human Gro-beta (also known as CXCL2) (SEQ ID NO: 22), human Gro-gamma (also known as CXCL3) (SEQ ID NO: 23), human ENA-78 (also known as CXCL5) (SEQ ID NO: 24), human GCP-2 (also known as CXCL6) (SEQ ID NO: 25), human NAP-2 (also known as CXCL7) (SEQ ID NO: 26), and human IL-8 (also known as CXCL58) (SEQ ID NO: 27). Collectively, all seven human ELR$^+$ CXC chemokines are called "human pan-ELR$^+$ CXC chemokines" herein.

The term "antibody," as used herein, is intended to refer to monoclonal immunoglobulin molecules comprising four polypeptide chains, two heavy (H) chains and two light (L) chains inter-connected by disulfide bonds. Each heavy chain comprises a heavy chain variable region (HCVR) and a heavy chain constant region. The heavy chain constant region comprises three domains, CH1, CH2, and CH3. Each light chain is comprised of a light chain variable region (LCVR) and a light chain constant region, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The CDR regions in HCVR are termed HCDR1, HCDR2, and HCDR3. The CDR regions in LCVR are termed LCDR1, LCDR2, and LCDR3. The CDRs contain most of the residues which form specific interactions with the antigen. There are currently three systems of CDR assignments for antibodies that are used for sequence delineation. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. For the purposes of the present invention, a hybrid of the Kabat and Chothia definitions are used to define CDRs. The assignment of amino acids in the HCVR and LCVR regions is in accordance with the Kabat numbering convention. It is further understood that the term "antibody" encompasses any cellular post-translational modifications to the antibody including, but not limited to, acylation and glycosylation.

As used herein, the term "septa-specific antibody" is intended to encompass an antibody that binds all seven human ELR$^+$ CXC chemokines with high affinity (e.g., with binding affinity ($K_D$) in the range of from about $5\times10^{-11}$ M to about $1\times10^{-9}$ M).

As used herein, a "patient" refers to a mammal, preferably a human with a disease, disorder, or condition that would benefit from a decreased level of human ELR$^+$ CXC chemokines or decreased bioactivity induced by human ELR$^+$ CXC chemokines.

As used herein, "treatment" or "treating" is intended to refer to all processes wherein there may be a slowing, controlling, or stopping of the progression of the disorders disclosed herein, but does not necessarily indicate a total elimination of all disorder symptoms. Treatment includes administration of an antibody of the present invention for treatment of a disease or condition in a patient, particularly in a human.

The antibodies disclosed herein bind human pan-ELR$^+$ CXC chemokines with high affinity. For example, the present antibodies bind all seven human ELR$^+$ CXC chemokines with a binding affinity ($K_D$) in the range of from about $5\times10^{-11}$ M to about $1\times10^{-9}$ M, for example from about $1.0\times10^{-10}$ M to about $8.6\times10^{-10}$ M, as measured by surface plasmon resonance, when expressed as a full-length IgG4 antibody. The present antibodies are further characterized in that while they bind human pan-ELR$^+$ CXC chemokines with specificity, they do not specifically bind to other CXC chemokines, for example stromal cell-derived factor-1 alpha (SDF-1α, also known as CXCL12).

In an embodiment, the antibodies of the invention can have a heavy chain variable region and a light chain variable region, wherein the heavy chain variable region comprises CDR regions with the following amino acid sequences: HCDR1 (SEQ ID NO: 10), HCDR2 (SEQ ID NO: 11), and HCDR3 (SEQ ID NO: 12); and wherein the light chain variable region comprises CDR regions with the following amino acid sequences: LCDR1 (SEQ ID NO: 7), LCDR2 (SEQ ID NO: 8) and LCDR3 (SEQ ID NO: 9).

In another embodiment, the antibodies of the invention can have a heavy chain variable region and a light chain variable region, wherein the heavy chain variable region comprises CDR regions with the following amino acid sequences: HCDR1 (SEQ ID NO: 10), HCDR2 (SEQ ID NO: 11), and HCDR3 (SEQ ID NO: 19); and wherein the light chain variable region comprises CDR regions with the following amino acid sequences: LCDR1 (SEQ ID NO: 7), LCDR2 (SEQ ID NO: 8) and LCDR3 (SEQ ID NO: 9).

In a further embodiment, the antibodies of the invention can comprise a heavy chain variable region having the amino acid sequence of SEQ ID NO: 2 or 14, and a light chain variable region having the amino acid sequence of SEQ ID NO: 4 or 16.

In yet a further embodiment, the antibodies of the invention can comprise a heavy chain having the amino acid sequence of SEQ ID NO: 1 or 13, and a light chain having the amino acid sequence of SEQ ID NO: 3 or 15.

Preferably, the antibodies comprise two identical light chains and two identical heavy chains. Preferably, the light chain with amino acid sequence as shown in SEQ ID NO: 3 is encoded by a nucleic acid comprising the polynucleotide sequence shown in SEQ ID NO: 6. Preferably, the heavy chain with amino acid sequence as shown in SEQ ID NO: 1 is encoded by a nucleic acid comprising the polynucleotide sequence shown in SEQ ID NO: 5. Preferably, the light chain amino acid sequence as shown in SEQ ID NO: 15 is encoded by a nucleic acid comprising the polynucleotide sequence shown in SEQ ID NO: 18. Preferably, the heavy chain amino acid sequence as shown in SEQ ID NO: 13 is encoded by a nucleic acid comprising the polynucleotide sequence shown in SEQ ID NO: 17.

The most preferred embodiment of the invention is an antibody comprising two identical heavy chains having the amino acid sequence of SEQ ID NO: 1, and two identical light chains having the amino acid sequence of SEQ ID NO: 3.

Antibodies of the present invention can be incorporated into pharmaceutical compositions suitable for administration to a patient. Typically the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Pharmaceutically acceptable carriers may further comprise minor amounts of auxiliary substances that enhance the shelf life or effectiveness of the antibody.

The compositions of this invention may be in a variety of forms. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, or intramuscular). In an embodiment, the antibody is administered by intraperitoneal or subcutaneous injection. However, as will be appreciated by the skilled artisan, the route and/or mode of administration will vary depending upon the desired results.

Supplementary active compounds can also be incorporated into the pharmaceutical compositions. In certain embodiments, an antibody of the invention is co-formulated with and/or co-administered with one or more additional therapeutic agents that are useful for treating disorders in which ELR$^+$ CXC chemokine activity is detrimental. For example, an antibody of the invention may be co-formulated and/or co-administered with one or more chemotherapy agents (e.g., sunitinib or cisplatin).

The pharmaceutical compositions of the invention may include a "therapeutically effective amount" of an antibody of the invention. A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects.

Dosage regimens may be adjusted to provide the optimum desired response (e.g., a therapeutic response). For example, a single bolus may be administered, several divided doses may be administered over time, or the dose may be proportionally reduced or increased as indicated by the exigencies of the therapeutic situation.

Dosage values may vary with the type and severity of the condition to be alleviated. It is further understood that for any particular subject, specific dosage regimens should be adjusted over time according to the individual need and the professional judgment of the person administering or supervising the administration of the compositions.

Specific binding of and neutralization by an antibody disclosed herein to human ELR$^+$ CXC chemokines allows said antibody to be used as a therapeutic for diseases and disorders which benefit from inhibition of human ELR$^+$ CXC chemokine bioactivity. Given their ability to bind and neutralize all seven human ELR$^+$ CXC chemokines, antibodies of the present invention offer advantages over monotherapies targeting single human ELR$^+$ CXC chemokines and combination therapies targeting multiple human ELR$^+$ CXC chemokines.

In an embodiment, the invention provides a method for treating ulcerative colitis or cancer, such as renal cancer or ovarian cancer. In another embodiment, the invention provides an antibody for use in treating ulcerative colitis or cancer, such as renal cancer or ovarian cancer.

This invention is further illustrated by the following non-limiting examples.

EXAMPLES

Expression and Production of Antibodies

Antibodies of the present invention can be expressed and purified as follows. An expression vector containing the DNA sequence of SEQ ID NO: 5 (encoding a heavy chain polypeptide of SEQ ID NO: 1) and SEQ ID NO: 6 (encoding a light chain polypeptide of SEQ ID NO: 3) is used to transfect NSO cells. An antibody resulting from this expression vector is "Antibody 1."

Additionally, an expression vector containing the DNA sequence of SEQ ID NO: 17 (encoding a heavy chain polypeptide of SEQ ID NO: 13) and SEQ ID NO: 18 (encoding a light chain polypeptide of SEQ ID NO: 15) is used to transfect NSO cells. An antibody resulting from this expression vector is "Antibody 2."

For either Antibody 1 or Antibody 2, transfected pools are plated at low density to allow for close-to-clonal outgrowth of stable expressing cells. The masterwells are screened for antibody expression and then scaled up in serum-free, suspension cultures to be used for production. Clarified media, into which the antibody has been secreted, is applied to a Protein A or G column that has been equilibrated with a compatible buffer, such as phosphate buffered saline (pH 7.4). The column is washed to remove nonspecific binding components. The bound antibody is eluted by pH gradient (such as 0.1 M sodium phosphate buffer pH 6.8 to 0.1 M sodium citrate buffer pH 2.5). Antibody fractions are detected by SDS-PAGE and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps may be greater than 99%. The product may be immediately frozen at −70° C. or may be lyophilized.

Binding Affinity to Human ELR$^+$ CXC Chemokines

Biacore 2000 instrument and Biacore 2000 Evaluation Software Version 4.1 are used for surface plasmon resonance analysis. A CM5 chip is prepared using manufacturer's EDC/NHS amine coupling method. Briefly, the surfaces of all four flow cells are activated by injecting a 1:1 mixture of EDC/NHS for 7 minutes at 10 µL/min Protein A is diluted to 100 µg/mL in 10 mM acetate, pH 4.5 buffer, and immobilized to achieve approximately 10,000 RU onto all 4 flow cells by 7-minute injection at a flow rate of 10 µL/minute. Unreacted sites are blocked with a 7-minute injection of ethanolamine at 10 µL/minute. Two injections of glycine (pH 1.5) for 30 seconds at 10 µL/minute are used to remove any non-covalently associated protein. Running buffer is HBS-EP+.

Antibody 1 or Antibody 2 is diluted to 2 µg/mL in running buffer, and approximately 400-600 RU is captured in flow cell (Fc). Ligands are diluted from 100 µg/mL to 50 nM in running buffer and then two-fold serially diluted in running buffer to 3.125 nM. Duplicate injections of each ligand concentration are injected at 100 µL/min for 150 seconds followed by a dissociation phase. The dissociation phase is 1800 seconds for all ligands. Regeneration is performed by injecting 10 mM glycine (pH 1.5) for 60 seconds at 50 µL/min over all flow cells. Reference-subtracted data is collected as Fc2-Fc1, Fc3-Fc1, and Fc4-Fc1. The measurements are obtained at 25° C. The on-rate ($k_{on}$) and off-rate ($k_{off}$) for each ligand are evaluated using a "1:1 (mass transfer) Binding" binding model. The affinity ($K_D$) is calculated from the binding kinetics according to the relationship: $K_D = k_{off}/k_{on}$.

The human ELR$^+$ CXC chemokines produce a concentration-dependent binding response with Antibody 1 and Antibody 2. Tables 1 and 2 summarize the $k_{on}$, $k_{off}$, and $K_D$ values for Antibody 1 and Antibody 2. These results demonstrate that Antibody 1 and Antibody 2 bind all seven human ELR$^+$ CXC chemokines with high affinity.

TABLE 1

In Vitro Binding Affinities to Human ELR⁺ CXC Chemokines for Antibody 1

| Chemokine | $k_{on}$ (1/Ms) × 10⁵ | $k_{off}$(1/s) × 10⁻⁵ | $K_D$ (pM) |
|---|---|---|---|
| human CXCL1(Gro alpha) | 9.30 ± 0.45 | 10.50 ± 0.14 | 113 ± 4 |
| human CXCL2(Gro Beta) | 7.73 ± 0.86 | 13.15 ± 0.64 | 171 ± 11 |
| human CXCL3 (Gro gamma) | 7.16 ± 0.08 | 12.35 ± 1.06 | 172 ± 13 |
| human CXCL5 (ENA-78) | 5.43 ± 0.61 | 12.20 ± 0.00 | 226 ± 25 |
| human CXCL6 (GCP-2) | 7.07 ± 0.11 | 57.80 ± 3.68 | 818 ± 40 |
| human CXCL7 (NAP-2) | 9.00 ± 0.75 | 16.15 ± 1.77 | 181 ± 35 |
| human CXCL8 (IL-8) | 3.39 ± 0.03 | 13.00 ± 0.57 | 384 ± 13 |

TABLE 2

In Vitro Binding Affinities to Human ELR⁺ CXC Chemokines for Antibody 2

| Chemokine | $k_{on}$ (1/Ms) × 10⁵ | $k_{off}$(1/s) × 10⁻⁵ | $K_D$ (pM) |
|---|---|---|---|
| human CXCL1(Gro alpha) | 6.28 | 1.53 | 243 |
| human CXCL2 (Gro beta) | 1.14 | 2.05 | 180 |
| human CXCL3 (Gro gamma) | 4.65 | 1.76 | 379 |
| human CXCL5 (ENA-78) | 4.27 | 1.51 | 354 |
| human CXCL6 (GCP-2) | 7.19 | 6.11 | 849 |
| human CXCL7 (NAP-2) | 5.21 | 2.18 | 418 |
| human CXCL8 (IL-8) | 2.61 | 1.24 | 473 |

Physical Stability Evaluation

Protein aggregation and self-association is an undesirable property in antibodies as it could potentially exacerbate unwanted effects, such as triggering an immune response. Thus, maintaining the antibody in a monomeric state is highly desirable. Percent high molecular weight (% HMW) aggregate is an indicator of protein aggregation and self-association. A higher % HMW aggregate indicates increased protein aggregation/self-association and increased physical instability. Physical stability of Antibody 1 and Antibody 2 are determined as follows.

Antibody is dialyzed overnight at 4° C. into 10 mM Citrate, pH 6+/−150 mM NaCl. The next morning, the samples are concentrated to 50 mg/mL, filtered through 0.2 micron filters, and then Tween-80 is added to a final concentration of 0.02%. Each sample is incubated at 25° C. for the specified times. Soluble aggregate formation is followed by analytical SEC using a TSK3000SWXL, 5 micron column with dimensions 30 cm×0.78 cm. The mobile phase is 50 mM Sodium Phosphate, pH 7, 175 mM NaCl, at a flow rate of 0.5 mL/min Samples are applied as 1 µL injections and monitored at 280 nm to determine the increase % HMW aggregate (Table 3).

The 50 mg/mL formulations are incubated for 1 and 4 weeks at 25° C. to assess longer-term stability under stress conditions. The delta % HMW aggregate is determined by subtracting the % HMW aggregate at time zero (designated as 'Initial' in Table 3) from the % HMW at the 1 week or 4 week time point. After 1 and 4 weeks, both Antibody 1 and Antibody 2 demonstrated delta % HMW below 1%, thus demonstrating good physical stability.

TABLE 3

| | Initial (4° C.) | 50 mg/mL % HMW (t = 1 week) | 50 mg/mL % HMW (t = 4 weeks) |
|---|---|---|---|
| % High Molecular Weight Aggregate | | | |
| Antibody 1 | | | |
| 10 mM Citrate pH7, 150 mM NaCl 25° C. | 0.78% | 1.24% | 1.41% |
| Δ % HMW | | 0.46% | 0.63% |
| 10 mM Citrate pH7, 150 mM NaCl, 0.02% Tween-80 25° C. | 1.05 | 1.46% | 1.75% |
| Δ % HMW | | 0.41% | 0.7% |
| Antibody 2 | | | |
| 10 mM Citrate pH7, 150 mM NaCl 25° C. | 0.37% | 0.48% | 0.59% |
| Δ % HMW | | 0.11% | 0.22% |
| 10 mM Citrate pH7, 150 mM NaCl, 0.02% Tween-80 25° C. | 0.42% | 0.55% | 0.74% |
| Δ % HMW | | 0.13% | 0.32% |

Antibody Epitope Mapping for Antibody I

Multiple approaches are undertaken to characterize the epitope for Antibody 1, including Western blot analysis, co-crystallization of the antibody with several ELR⁺ CXC chemokines, and mutational analysis for binding and neutralization.

Western Blot Analysis

To determine if Antibody 1 is able to bind a linear or conformational epitope, Western blot analysis is performed using reducing and non-reducing conditions. Electrophoresis of the proteins is performed using pre-cast NuPAGE® 4-12% Bis-Tris gels. NuPAGE® MES SDS running buffer is added to both the inner (200 mL) and outer (at least 600 mL) chambers of the mini-cells. Serial dilutions of human CXCL8 (400 ng, 100 ng, or 25 ng per lane) are made in NuPAGE® LDS 4× Sample Buffer with or without NuPAGE® 10× Sample Reducing Agent. Samples are heated at 95° C. for 2 minutes. Load volumes are 10 µL per lane for the samples, and 5 µL per lane for the SeeBlue Plus2 Prestained Standard marker. The gels are run at 200V for 35 minutes at room temperature.

Proteins are transferred to PVDF using the iBlot® Dry Blotting System with iBlot® Transfer Stack, Nitrocellulose, Mini. The membrane is blocked in blocking solution (3% nonfat milk in phosphate buffered saline) for 1 hour at room temperature. Antibody 1 is added to the blocking solution to a final concentration of 1 µg/mL and then is incubated for 2 hours at room temperature. Following primary incubation, the antibody/block solution is removed, and the membrane is washed 3 times for 15 minutes in wash buffer (phosphate buffered saline+0.05% Tween 20). The membrane is then incubated with HRP conjugated donkey anti-human Fc specific IgG secondary antibody (0.1 µg/mL in blocking solution) for 1 hour at room temperature. After removal of the secondary antibody, the membrane is washed 4 times for 10 minutes with wash buffer. The membrane is then incubated with working solution of the Stable Peroxide Solution and the Luminol/Enhancer Solution (Super Signal West Pico Chemiluminescent Substrate) for 5 minutes. The membrane is placed in a plastic membrane protector in an X-ray film cassette with CL-X Posure™ Film for 30 seconds. Film is developed using a Konica SRX-101 system.

Under non-reducing conditions, at a CXCL8 concentration of 400 ng, two bands appeared at about 17 kDa and about 10 kDa. At a CXCL8 concentration of 100 ng, one band appeared at about 10 kDa. At a CXCL8 concentration of 25 ng, no bands appeared. Under reducing conditions, no bands appeared at any of the tested concentrations.

The results demonstrated that Antibody 1 is able to bind non-reduced, denatured human CXCL8, but is unable to bind reduced, denatured human CXCL8. Therefore, the two disulfide bonds in CXCL8 are needed to maintain the antibody epitope. These results demonstrate a conformational epitope for Antibody 1.

Crystal Structure Analysis

Crystal structures of the Fab/antigen complexes for human CXCL8, and cynomolgus monkey CXCL2, CXCL3, and CXCL7 are obtained to determine the complete binding surface of Antibody 1. Wild type truncated human CXCL8 1-66, human CXCL8 point mutants, and cynomolgus monkey CXCL7 are all expressed in E. coli with N-terminal His-SUMO tags. These proteins are refolded; the tags are cleaved; and the proteins are purified by standard purification techniques. Cynomolgus monkey CXCL2 and CXCL3 are expressed in HEK293 EBNA cells and are purified by standard purification techniques. Formation of disulfide bonds is confirmed by tryptic digest and mass fingerprint analysis, and activity is confirmed by neutrophil chemotaxis assay. A Fab of Antibody 1 is expressed in HEK293 EBNA cells and is purified by standard purification techniques. Fab/antigen complexes are formed by adding slight molar excess of antigen to the Fab, followed by size exclusion chromatography purification to remove excess free antigen. Complexes are crystallized, and the crystal structures are solved by molecular replacement using Buster 2.9.5 (Global Phasing Ltd.).

These crystal structures confirmed that the epitope for Antibody 1 included the N-terminus of the ELR$^+$ CXC chemokines, but they also showed contacts between the Fab and the β1-β2 loop and the β2 and β3 strands of the ELR$^+$ CXC chemokines. The crystal structures also demonstrate that the antibody specifically recognizes the fold of the ELR$^+$ CXC chemokines, since the crystal structures were superimposable. Numerous hydrogen bonding and Van der Waals interactions were also observed. Most notably, the conserved R6 side chain of the ELR motif sat in a deep binding pocket formed by the Fab heavy chain at residues W33, Y102, and Y110, and the Fab light chain at residue W94. The wild type truncated human CXCL8 chemokine also hydrogen bonds with both the Fab heavy chain at residue E99 and the Fab light chain at the N91 backbone carbonyl. Other hydrogen bonds observed were between the L5 backbone carbonyl of the wild type truncated human CXCL8 chemokine and the Fab light chain W94 backbone amide; the I10 backbone carbonyl of the wild type truncated human CXCL8 chemokine and the Fab heavy chain S52 side chain; the K11 side chain of the wild type truncated human CXCL8 chemokine and the Fab heavy chain T30 and S31 side chains; the H33 side chain of the wild type truncated human CXCL8 chemokine and the Fab light chain W94 backbone carbonyl; the A35 backbone amide and the Fab heavy chain N59 side chain; and the C50 backbone amide of the wild type truncated human CXCL8 chemokine and the Fab heavy chain Y104 backbone carbonyl. Further, the N-terminal residues 5 through 13 of the wild type truncated human CXCL8 chemokine made numerous contacts with the Fab as the N-terminus sat in a groove between the Fab heavy chain CDR2 and CDR3. Additionally, the Fab heavy chain CDR3 loop extended away from this groove and interacted with the non-N-terminal residue I40 on the β2 strand, and residues Glu48, Leu49, and Cys50 on the β3 strand of the wild type truncated human CXCL8 chemokine. Finally, residues 33-36 of the β1-β2 loop in the wild type truncated human CXCL8 chemokine packs against the Fab heavy chain CDR2.

Mutational Analysis

Several key contacts between the Antibody 1 Fab and wild type human CXCL8 are observed in the crystal structure and are further tested through binding kinetic studies and U937-huCXCR2 fluorescent imaging plate reader (FLIPR) neutralization of human CXCL8 point mutants. To study these key contacts, several point mutants (R6A, I10A, A35P, I40A, and L49A) are made based on the human CXCL8 sequence (SEQ ID NO: 27). Wild type, R6A, I10A, A35P, I40A, and L49A human CXCL8 point mutants are expressed, refolded, and purified according to standard techniques. Formation of disulfide bonds is confirmed by tryptic digest and mass fingerprint analysis, and activity is confirmed by neutrophil chemotaxis assay.

Binding kinetics are tested on a Biacore 2000 instrument with Biacore 2000 Evaluation Software Version 4.1 as described above.

Wild type and mutant human CXCL8 are tested for biologic activity and for neutralization by Antibody 1 using the U937-huCXCR2 assay. U937-huCXCR2 is a monocytic cell line transduced with retrovirus for expression of human CXCR2. A description of the U937-huCXCR2 assay is found below under Neutralizing Assays.

CXCL8 mutants are serially diluted in Assay Buffer containing 0.2% BSA in wells of v-bottom 96-well polypropylene plates. Ligand concentrations are 3 times the final assay concentration (final assay concentrations range from 300 to 0.0051 nM). A cell plate and a ligand plate are loaded into a <u>F</u>luorescent <u>I</u>maging <u>P</u>late <u>R</u>eader (FLIPR-3, Molecular Devices) programmed to transfer 50 μL of ligand to wells of the cell plate. Fluorescence is recorded at 1 second intervals for 90 seconds. The change in fluorescence [delta relative fluorescence units (DRFU), Max RFU-Min RFU] is calculated from images 10 to 90. DRFU versus log (ligand concentration) is plotted and $EC_{50}$ values are determined by nonlinear regression using Graph Pad Prism. Assays are performed in triplicate over three assay plates.

Antibody 1 is serially diluted in Assay Buffer containing 0.2% BSA. Antibody concentrations are 3 times the final assay concentration (final concentrations range from 10 to 0.0195 μg/ml). Stock solutions of wild type human CXCL8 and CXCL8 mutants are prepared in Assay Buffer+0.2% BSA at 240 nM (30× the final assay concentration of 8 nM). 20 μL of ligand is mixed with 180 μL of Antibody 1 in wells of v-bottom 96-well polypropylene plates. Ligand and antibody are incubated at room temperature for 30 minutes. A cell plate and a ligand-antibody plate are loaded into a <u>F</u>luorescent <u>I</u>maging <u>P</u>late <u>R</u>eader (FLIPR-3, Molecular Devices) programmed to transfer 50 μL of ligand-antibody to wells of the cell plate. Fluorescence is recorded at 1 second intervals for 90 seconds. The change in fluorescence (DRFU) is calculated from images 10 to 90. DRFU versus log (antibody concentration) is plotted and $IC_{50}$ values are determined by nonlinear regression using Graph Pad Prism. Assays are performed in triplicate over three assay plates.

The binding kinetics, biologic activity, and neutralization results are summarized in Table 4. The affinity measurements are obtained at 25° C. The on-rate ($k_{on}$) and off-rate ($k_{off}$) for each ligand are evaluated using a "1:1 (mass transfer) Binding" binding model. The affinity ($K_D$) is calculated from the binding kinetics according to the relationship: $K_D = k_{off}/k_{on}$.

Several of the mutations knocked out activity to the receptor ($EC_{50}$) and, therefore, could not be tested for neutralization. It is noted that the A35P mutation completely abolished neutralizing activity despite having full activity to the receptor. These results highlight key contacts (R6, I10, A35, I40, and L49) within the binding interface of the CXCL8 antigen that are important for antibody binding.

TABLE 4

Binding kinetics, U937 FLIPR activity ($EC_{50}$), and U937 FLIPR neutralization ($IC_{50}$) of human CXCR8 wild type and mutants.

| Variant | $k_{on}$ (M$^{-1}$ s$^{-1}$) | $k_{off}$ (s$^{-1}$) | $K_D$ (pM) | $EC_{50}$ (µg/mL) | $IC_{50}$ (µg/mL) |
|---|---|---|---|---|---|
| WT | $3.03 \pm 3.78 \times 10^6$ | $4.41 \pm 4.55 \times 10^{-4}$ | $236 \pm 144$ | $1.3 \pm 0.8$ (n = 4) | 0.9 |
| R6A | | No Binding | | Not Active | |
| I10A | $2.77 \pm 0.39 \times 10^5$ | $3.44 \pm 0.01 \times 10^{-4}$ | $1260 \pm 184$ | Not Active | |
| A35P | $1.06 \pm 0.07 \times 10^6$ | $4.97 \pm 1.72 \times 10^{-3}$ | $4740 \pm 1920$ | $1.9 \pm 0.3$ (n = 2) | No neutralization |
| I40A | $1.61 \pm 0.21 \times 10^4$ | $4.24 \pm 1.16 \times 10^{-4}$ | $27100 \pm 10700$ | Not Active | |
| L49A | $1.43 \pm 0.24 \times 10^5$ | $5.44 \pm 0.42 \times 10^{-4}$ | $3830 \pm 354$ | $5.6 \pm 1.3$ (n = 2) | 1.5 |

Overall, the epitope mapping analysis for Antibody 1 demonstrated that the binding interface of the antigen includes the N-terminus of the ELR$^+$ CXC chemokines (amino acids 5-13), the β1-β2 loop (amino acids 33-36), and the β2 and β3 strands (amino acids 40, 48-50). Key contacts within this interface that are important for antibody binding include the amino acids R6, I10, A35, I40, and L49 in CXCL8 (SEQ ID NO: 27).

Neutralization Assays

In Vitro Neutralization of Human ELR$^+$ CXC Chemokines Using Human CXCR2-Transfected HMEC Cells Since all of the ELR$^+$ CXC chemokines can bind CXCR2 receptor, cells expressing CXCR2 were selected for in vitro studies. HMEC-huCXCR2 is an immortalized human endothelial cell line transduced with retrovirus for expression of human CXCR2 receptor. HMEC cells expressing human CXCR2 are able to induce intracellular Ca$^{2+}$ influx in response to human, cynomolgus monkey, rat, and mouse ELR$^+$ CXC chemokines. Intracellular Ca$^{2+}$ influx can be detected by a Fluorescent Imagine Plate Reader (FLIPR). Chemokine neutralization should therefore also neutralize intracellular Ca$^{2+}$ influx induced by these chemokines.

HMEC-huCXCR2 is maintained in MCDB 31 medium supplemented with 10% fetal bovine serum, 2× GlutaMax, 1× non-essential amino acids, 1 µg/mL hydrocortisone, 10 ng/mL human Epidermal Growth Factor, and 0.4 µg/mL puromycin at 37° C. in 5% CO$_2$. Cultures are maintained at sub-confluent densities (50-80% confluent). Cells are harvested with TrypLE Express, cell density is adjusted to 3×10$^5$ cells/mL in complete culture medium, and 100 µL of the cell suspension are seeded into wells of black clear-bottom assay plates. Cell plates are incubated at room temperature for 30 minutes to allow cells to settle to the bottom of the wells before plates are incubated overnight at 37° C. in 5% CO$_2$. For each assay plate, the contents of one vial of Fluo-4NW reagent is suspended in 10 mL Assay Buffer and 100 µL probenecid to make 1× Fluo-4NW reagent. After incubation, culture medium is aspirated and 100 µL of the 1× Fluo-4NW solution is added to each well of the assay plate. Plates are incubated for 30 minutes at 37° C., followed by an additional 30 minutes at room temperature and protected from light. Antibody 1 is serially diluted in Assay Buffer containing 0.2% BSA. Antibody concentrations are 3× the final assay concentration (final concentrations range from 10-0.0195 µg/mL). Stock solutions of ligands are prepared in Assay Buffer+0.2% BSA at 300 nM (30× the final assay concentration of 10 nM). 20 µL of ligand is mixed with 180 µL of antibody in wells of v-bottom 96-well polypropylene plates. Ligand and antibody are incubated at room temperature for 30 minutes. A cell plate and a ligand-antibody plate are loaded into a Fluorescent Imagine Plate Reader (FLIPR-3, Molecular Devices) programmed to transfer 50 µL of ligand-antibody to wells of the cell plate. Fluorescence is recorded every second for 90 seconds. The change in fluorescence (DRFU) is calculated from images 10 to 90. DRFU versus log (antibody concentration) is plotted and $IC_{50}$ values are determined by nonlinear regression using Graph Pad Prism. Assays are performed in triplicate over three assay plates. Data are expressed as the mean of replicates.

The results are summarized in Table 5. These results demonstrate that Antibody 1 was able to neutralize all seven human ELR$^+$ CXC chemokines. $IC_{50}$ values are expressed as µg/mL of antibody (standard deviations are in parentheses). Both the 72 amino acid and 77 amino acid forms of CXCL8 were used. Data are average of 2-5 replicates.

TABLE 5

In vitro FLIPR study using HMEC cells expressing human CXCR2

| | $IC_{50}$ (µg/mL) |
|---|---|
| CXCL1 | 0.867 (±0.153) |
| CXCL2 | 1.281 (±0.449) |
| CXCL3 | 0.731 (±0.187) |
| CXCL5 | 0.681 (±0.347) |
| CXCL6 | 1.122 (±0.523) |
| CXCL7 | 1.068 (±0.324) |
| CXCL8 (72) | 0.951 (±0.416) |
| CXCL8 (77) | 0.358 (±0.078) |

In Vitro Neutralization of Human CXCL8 or CXCL1-Induced Chemotaxis Using Primary Human Neutrophils A chemotaxis assay using human neutrophils was chosen to determine the neutralizing activity of Antibody 1 in cells naturally expressing both CXCR1 and CXCR2. Peripheral blood from healthy volunteers is drawn into two 10 mL sodium heparin tubes. To isolate neutrophils, 5 mL of blood is layered over 5 mL of Polymorphprep in four 15 mL tubes. The tubes are centrifuged for 30 minutes at 470×g, 18° C. The plasma and top cell band (mononuclear cells) are removed and discarded. The second band (neutrophils) is pooled from the 4 tubes and an equal volume of PBS is added. The tube is centrifuged for 10 minutes at 400×g, 18° C. The pellet is washed with 12 mL of PBS, centrifuged as before, and the pellet is re-suspended with 11 mL HBSS/BSA (7.5 mg/mL BSA, HBSS). 60×10$^6$ cells are suspended in 12 mL HBSS/BSA and 5 µM CMFDA and incubated for 30 min at 37° C. Post-incubation, the tube is centrifuged to pellet the cells, washed one time with 12 mL HBSS/BSA, and then the cells are re-suspended in 12 mL HBSS/BSA (5×10$^6$ cells/mL).

Antibody 1 and isotype control (human IgG4 antibody) are diluted to 1495 nM using HBSS/BSA (Dilution 1) and then serially diluted 1:5 with HBSS/BSA. CXCL8 is diluted to 20 nM with HBSS/BSA. CXCL1 is diluted to 10.1 nM with HBSS/BSA.

70 µL of Antibody 1 or HBSS/BSA are mixed with 70 µL of either the CXCL8 or CXCL1 solution and incubated at room temperature for ~30 minutes. 30 µL of the mixture are dispensed into the lower chamber wells of a ChemoTx plate in triplicate. Wells containing only HBSS/BSA (no chemokine or antibody) will show the background signal. The ChemoTx filter is placed over the lower chamber and 50 µL (250,000 cells) is dispensed above each well. The ChemoTx plate is incubated for 3 hours at 37° C., 5% $CO_2$. After incubation, the cells are rinsed from the top surface with PBS and the ChemoTx filter is removed. Fluorescence is read (Wallac Victor$^3$ 1420 counter) 485/535 using only the bottom detector. The mean fluorescence of the background wells (HBSS/BSA only) is subtracted from the test well fluorescence, and the mean and standard deviations are calculated in Excel.

At a CXCL8 concentration of 5 nM, the $IC_{50}$ for Antibody 1 (MW 150,000 kDa) was 26.4 (±0.236) nM. At a CXCL8 concentration of 10 nM, the $IC_{50}$ for Antibody 1 was 43.7 (±0.086) nM. At a CXCL1 concentration of 5 nM, the $IC_{50}$ for Antibody 1 was 18.5 (±0.158) nM. At a CXCL1 concentration of 20 nM, the $IC_{50}$ for Antibody 1 was 40.3 (±0.112) nM. At all tested concentrations of CXCL1 and CXCL8, the isotype control antibody did not affect chemotaxis. The data show that Antibody 1 can block the chemotactic activity of human CXCL8 or CXCL1 in a dose dependent manner while chemotactic activity was unaffected by the isotype control antibody.

In Vivo Acute DSS Colitis Model in Mice

Dextran sulfate sodium (DSS) is the most commonly used model of Ulcerative Colitis (UC). In this model, DSS is a chemical irritant that is added to drinking water to induce acute disease that resembles UC. The acute phase of DSS colitis is characterized by the recruitment of neutrophils to the mucosa and submucosa, and increased expression of $ELR^+$ CXC chemokines. However, chronic exposure to DSS causes severe gut damage and significant weight loss, which is not suitable in a colitis model. To accommodate the acute nature of this model, Antibody 1 was used in a prophylactic manner to test its ability to inhibit the recruitment of neutrophils and the development of colitis. Of note in this model, mouse CXCL5 (LIX) protein is significantly increased in colon tissue (Kwon 2005); however, Antibody 1 does not neutralize this mouse chemokine.

C57BL/6 mice, 8-10 wks old, weighing 18-22 g, are obtained. Blood is collected by cardiac puncture and analyzed to establish a baseline. To induce colitis, mice receive 2.5% DSS (MW=36,000-50,000) in the drinking water for 5 days (Days 1-5) followed by 6 days of no DSS water (reflecting acute inflammation). Control healthy mice receive water only ("no DSS" group). Mice receiving DSS are dosed by subcutaneous injection on Day 0, 2, 4, and 8 with human IgG4 control antibody (25 mg/kg) or Antibody 1 (25 mg/kg). Body weight is recorded daily. The number of mice used for each treatment is 9 (except 5 healthy mice are used in the healthy "no DSS" group.) The study is performed in quadruplicate.

As shown in Table 6, DSS mice that received human IgG4 control antibody lost weight dramatically between Day 5 and Day 8. DSS mice that received Antibody 1 before induction of colitis and during the acute phase of the disease displayed less weight loss between Day 5 and Day 8 than those DSS mice treated with human IgG4 control antibody (94.0% initial body weight for Antibody 1 versus 85.3% initial body weight for IgG4 control on Day 8). These results demonstrate that systemic administration of Antibody 1 effectively mitigated weight loss in DSS-induced colitis, supporting the conclusion that Antibody 1 neutralizes the activity of certain mouse $ELR^+$ CXC chemokines and decreases neutrophil recruitment to the colon.

TABLE 6

| | % of Initial Body Weight | | |
| --- | --- | --- | --- |
| Day | No DSS | IgG4 | Antibody 1 |
| 1 | 104.4 | 99.9 | 100.0 |
| 2 | 103.9 | 99.8 | 102.9 |
| 3 | 103.0 | 100.3 | 101.4 |
| 4 | 101.0 | 99.5 | 100.9 |
| 5 | 101.2 | 97.5 | 96.9 |
| 8 | 102.2 | 85.3 | 94.0 |
| 9 | 99.8 | 89.6 | 93.5 |
| 10 | 100.7 | 93.7 | 93.6 |
| 11 | 101.3 | 98.2 | 97.0 |

In Vivo Neutralization in 786-O Clear Cell Renal Cell Xenograft Model

786-O renal cell carcinoma (RCC) cells are mixed 1:1 with matrigel and implanted subcutaneously in the right rear flank of athymic nude female mice at $3.0 \times 10^6$ cells per injection. 786-O xenograft-bearing mice having tumor volumes that reached 100 mm$^3$ were orally gavaged with 10 mg/kg of sunitinib two times a day under a continuous dosing regimen until the mice started progressing with tumor growth even under sunitinib treatment like control-treated mice (IgG4 and 10% vehicle). Mice that were progressing with tumor growth on sunitinib therapy were randomly divided into 2 groups. One group receives sunitinib at 10 mg/kg two times a day plus control IgG4 antibody at 20 mg/kg once a week. The other group receives suninitib at 10 mg/kg two times a day plus Antibody 1 at 20 mg/kg once a week. Average tumor volumes (standard error in parentheses) are shown in Table 7. The addition of Antibody 1 to sunitinib treatment reduced tumor growth significantly over time (p<0.0001), indicating that Antibody 1 resensitized clear cell RCC tumors to sunitinib treatment.

TABLE 7

| | Average Tumor Volume (mm$^3$) | | |
| --- | --- | --- | --- |
| Day | IgG4 and 10% vehicle | IgG4 and Sunitinib | Antibody 1 and Sunitinib |
| 11 | 82.84 (±18.52) | 73.21 (±8.91) | 72.54 (±40.89) |
| 17 | 112.12 (±25.06) | 95.34 (±11.6) | 95.99 (±54.11) |
| 24 | 148.41 (±33.17) | 124.86 (±15.19) | 138.32 (±77.97) |
| 27 | 180.24 (±40.29) | 138.08 (±16.8) | 152.87 (±86.18) |
| 34 | 205.22 (±45.87) | 183.2 (±22.29) | 181.08 (±102.08) |
| 38 | 221.66 (±49.55) | 207.46 (±25.25) | 211.1 (±119) |
| 41 | 255.46 (±57.1) | 210.04 (±25.56) | 222.01 (±125.15) |
| 46 | 267.75 (±59.85) | 267.53 (±32.55) | 248.74 (±140.22) |
| 48 | 292.17 (±65.31) | 268.24 (±32.64) | 276.78 (±156.03) |
| 52 | 325.13 (±72.68) | 301.1 (±36.64) | 286.57 (±161.55) |
| 55 | 331.39 (±74.37) | 328.55 (±39.98) | 262.9 (±148.21) |
| 59 | 373.91 (±84.32) | 371.36 (±45.19) | 304.06 (±171.41) |
| 62 | 413.09 (±93.47) | 387.79 (±47.19) | 313.16 (±176.54) |
| 66 | 479.4 (±108.92) | 417.33 (±50.78) | 285.85 (±161.14) |
| 69 | 537.74 (±122.53) | 494.68 (±60.19) | 276.64 (±155.95) |
| 73 | 520.11 (±118.92) | 527.88 (±64.23) | 244.07 (±137.59) |
| 76 | 532.57 (±122.53) | 595.93 (±72.52) | 228.91 (±129.04) |
| 81 | 597.7 (±137.49) | 601.51 (±73.19) | 196.06 (±110.52) |
| 84 | 720.91 (±166.16) | 652.01 (±79.34) | 193.08 (±108.84) |
| 87 | 713.64 (±164.79) | 663.62 (±80.75) | 181.85 (±102.51) |
| 90 | 785.88 (±181.79) | 775.05 (±94.31) | 175.88 (±99.15) |
| 94 | 891.11 (±206.57) | 836.89 (±101.84) | 192.57 (±108.56) |
| 97 | 1073.86 (±249.3) | 1010.26 (±122.93) | 210.16 (±118.47) |

In Vivo Neutralization in SKOV3-Luc Ovarian Cancer Xenograft Model

SKOV3-Luc is a human ovary cancer cell line that expresses firefly luciferase gene. SKOV3-Luc cells are often used in vivo to establish human ovarian adenocarcinoma tumor growth.

SKOV3-Luc ovarian cancer cells were mixed 1:1 with matrigel and implanted subcutaneously in the right rear flank of athymic nude female mice at $3.0 \times 10^6$ cells per injection. Mice were randomized into 4 groups at baseline according to tumor volume after the xenografts were grown to an average tumor volume of 200 mm³ Mice received either control IgG4 antibody (2.5 mg/kg once a week), cisplatin (2.5 mg/kg once a week), Antibody 1 (20 mg/kg once a week), or a combination of cisplatin (2.5 mg·kg once a week) and Antibody 1 (20 mg/kg once a week) by intraperitoneal injection. Tumor growth is shown in Table 8. Cisplatin monotherapy did not show statistically significant tumor growth inhibition compared to isotype control. However, the combination of cisplatin and Antibody 1 showed statistically significant tumor growth inhibition ($p \leq 0.001$) compared to isotype control and cisplatin monotherapy, indicating that Antibody 1 synergistically augments chemotherapy in the SKOV3-Luc ovarian cancer xenograft model.

TABLE 8

| Day | Average Tumor Volume (mm³) | | | |
|---|---|---|---|---|
| | IgG4 | Cisplatin | Antibody 1 | Antibody 1 and Cisplatin |
| 14 | 128.45 (±7.25) | 122.65 (±12.2) | 109.35 (±12.7) | 127.17 (±26.72) |
| 19 | 182.92 (±10.33) | 190.65 (±18.97) | 173.95 (±20.2) | 167.94 (±35.29) |
| 22 | 269.83 (±15.23) | 289.15 (±28.77) | 234.58 (±27.25) | 218.81 (±45.98) |
| 26 | 507.66 (±28.66) | 484.72 (±48.23) | 364.42 (±42.33) | 349.81 (±73.51) |
| 32 | 904.66 (±51.07) | 806.31 (±80.23) | 739.26 (±85.86) | 530.63 (±111.5) |
| 35 | 1052.88 (±59.44) | 923.02 (±91.85) | 821.83 (±95.45) | 579.7 (±121.81) |
| 40 | 1143.39 (±64.55) | 941.42 (±93.68) | 1026.68 (±119.25) | 585.37 (±123) |
| 43 | 1382.03 (±78.03) | 1047.34 (±104.22) | 1098.72 (±127.61) | 626.99 (±131.75) |

We claim:

1. An antibody that binds human growth-regulated oncogene ("Gro")-alpha, human Gro-beta, human Gro-gamma, human epithelial neutrophil activating peptide-78, human granulocyte chemotactic protein-2, human neutrophil activating protein-2, and human interleukin-8, the antibody comprising a light chain and a heavy chain, wherein the light chain comprises a light chain variable region (LCVR) and the heavy chain comprises a heavy chain variable region (HCVR), wherein the LCVR comprises light chain complementarity determining regions ("LCDR") LCDR1, LCDR2, LCDR3 and the HCVR comprises heavy chain complementarity determining regions ("HCDR") HCDR1, HCDR2, HCDR3, wherein LCDR1 is RASQSISNNLH (SEQ ID NO: 7), LCDR2 is YTSRSVS (SEQ ID NO: 8), LCDR3 is GQN-NEWPEV (SEQ ID NO: 9), HCDR1 is GYEFTSYWIH (SEQ ID NO: 10), HCDR2 is NISPNSGSANYNEKFKS (SEQ ID NO: 11), and HCDR3 is EGPYSYYPSRX-aaYYGSDL (SEQ ID NO: 20) wherein Xaa is E or Q.

2. The antibody of claim 1, wherein the amino acid sequence of the HCVR is SEQ ID NO: 2 or SEQ ID NO: 14 and the LCVR is SEQ ID NO: 4 or 16.

3. The antibody of claim 1, wherein the amino acid sequence of the HCVR is SEQ ID NO: 2 and the amino acid sequence of the LCVR is SEQ ID NO: 4.

4. The antibody of claim 1, wherein the amino acid sequence of the heavy chain is SEQ ID NO: 1 and the amino acid sequence of the light chain is SEQ ID NO: 3.

5. The antibody of claim 1 comprising two heavy chains having the amino acid sequence of SEQ ID NO: 1, and two light chains having the amino acid sequence of SEQ ID NO: 3.

6. A DNA molecule comprising a polynucleotide sequence encoding a first polypeptide having the amino acid sequence of SEQ ID NO: 1 or 13; and comprising a second polynucleotide sequence encoding a polypeptide having the amino acid sequence of SEQ ID NO: 3 or 15.

7. The DNA molecule of claim 6, wherein the first polynucleotide sequence encodes a polypeptide having the amino acid sequence of SEQ ID NO: 1, and the second polynucleotide sequence encodes a polypeptide having the amino acid sequence of SEQ ID NO: 3.

8. A mammalian cell comprising the DNA molecule of claim 6, wherein the cell is capable of expressing an antibody comprising a light chain polypeptide having an amino acid sequence of SEQ ID NO: 3 or 15 and a heavy chain polypeptide having an amino acid sequence of SEQ ID NO: 1 or 13.

9. A process for producing an antibody comprising a light chain whose amino acid sequence is SEQ ID NO: 3 or 15 and a heavy chain whose amino acid sequence is SEQ ID NO: 1 or 13, the process comprising cultivating the mammalian cell of claim 8 under conditions such that the antibody is expressed, and recovering the expressed antibody.

10. An antibody produced by the process of claim 9.

11. A pharmaceutical composition comprising an antibody of claim 1 and one or more pharmaceutically acceptable carriers, diluents, or excipients.

12. A pharmaceutical composition comprising an antibody of claim 10 and one or more pharmaceutically acceptable carriers, diluents, or excipients.

* * * * *

```
SEQUENCE LISTING

<160> NUMBER OF SEQ ID NOS: 27

<210> SEQ ID NO 1
<211> LENGTH: 452
<212> TYPE: PRT
<213> ORGANISM: Artificial Sequence
<220> FEATURE:
<223> OTHER INFORMATION: synthetic construct

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Glu Phe Thr Ser Tyr
                20                  25                  30

Trp Ile His Trp Val Arg Gln Ala Pro Gly Gln Gly Leu Glu Trp Met
            35                  40                  45

Gly Asn Ile Ser Pro Asn Ser Gly Ser Ala Asn Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Ser Tyr Tyr Pro Ser Arg Glu Tyr Tyr Gly
                100                 105                 110

Ser Asp Leu Trp Gly Gln Gly Thr Leu Val Thr Val Ser Ser Ala Ser
            115                 120                 125

Thr Lys Gly Pro Ser Val Phe Pro Leu Ala Pro Cys Ser Arg Ser Thr
        130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175
```

```
His Thr Phe Pro Ala Val Leu Gln Ser Ser Gly Leu Tyr Ser Leu Ser
                180                 185                 190
Ser Val Val Thr Val Pro Ser Ser Leu Gly Thr Lys Thr Tyr Thr
            195                 200                 205
Cys Asn Val Asp His Lys Pro Ser Asn Thr Lys Val Asp Lys Arg Val
            210                 215                 220
Glu Ser Lys Tyr Gly Pro Pro Cys Pro Pro Cys Pro Ala Pro Glu Phe
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser Gln Glu Asp Pro Glu Val Gln Phe Asn Trp Tyr Val Asp Gly Val
            275                 280                 285
Glu Val His Asn Ala Lys Thr Lys Pro Arg Glu Glu Gln Phe Asn Ser
290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Gly Leu Pro Ser
                325                 330                 335
Ser Ile Glu Lys Thr Ile Ser Lys Ala Lys Gly Gln Pro Arg Glu Pro
                340                 345                 350
Gln Val Tyr Thr Leu Pro Pro Ser Gln Glu Met Thr Lys Asn Gln
            355                 360                 365
Val Ser Leu Thr Cys Leu Val Lys Gly Phe Tyr Pro Ser Asp Ile Ala
            370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Arg Leu
                405                 410                 415
Thr Val Asp Lys Ser Arg Trp Gln Glu Gly Asn Val Phe Ser Cys Ser
                420                 425                 430
Val Met His Glu Ala Leu His Asn His Tyr Thr Gln Lys Ser Leu Ser
                435                 440                 445
Leu Ser Leu Gly
    450

<210> SEQ ID NO 2
<211> LENGTH: 126
<212> TYPE: PRT
<213> ORGANISM: Artificial Sequence
<220> FEATURE:
<223> OTHER INFORMATION: synthetic construct

<400> SEQUENCE: 2

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Glu Phe Thr Ser Tyr
            20                  25                  30
Trp Ile His Trp Val Arg Gln Ala Pro Gly Gln Gly Leu Glu Trp Met
        35                  40                  45
Gly Asn Ile Ser Pro Asn Ser Gly Ser Ala Asn Tyr Asn Glu Lys Phe
    50                  55                  60
Lys Ser Arg Val Thr Met Thr Arg Asp Thr Ser Thr Ser Thr Val Tyr
65                  70                  75                  80
```

Met Glu Leu Ser Ser Leu Arg Ser Glu Asp Thr Ala Val Tyr Tyr Cys
                85                  90                  95

Ala Arg Glu Gly Pro Tyr Ser Tyr Tyr Pro Ser Arg Gly Tyr Tyr Gly
            100                 105                 110

Ser Asp Leu Trp Gly Gln Gly Thr Leu Val Thr Val Ser Ser
        115                 120                 125

<210> SEQ ID NO 3
<211> LENGTH: 214
<212> TYPE: PRT
<213> ORGANISM: Artificial Sequence
<220> FEATURE:
<223> OTHER INFORMATION: synthetic construct

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Thr Ser Arg Ser Val Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Gln Asn Asn Glu Trp Pro Glu
                85                  90                  95

Val Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 107
<212> TYPE: PRT
<213> ORGANISM: Artificial Sequence
<220> FEATURE:
<223> OTHER INFORMATION: synthetic construct

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Thr Ser Arg Ser Val Ser Gly Ile Pro Ala Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gly Gln Asn Asn Glu Trp Pro Glu
                 85                  90                  95

Val Phe Gly Gly Gly Thr Lys Val Glu Ile Lys
            100                 105

<210> SEQ ID NO 5
<211> LENGTH: 1356
<212> TYPE: DNA
<213> ORGANISM: Artificial Sequence
<220> FEATURE:
<223> OTHER INFORMATION: synthetic construct

<400> SEQUENCE: 5
caggtgcagc tggtgcagtc tggtgctgaa gtgaagaagc tggggcctc agtgaaggtg        60 tcctgcaagg catctggcta cgagttcacc agctactgga ttcactgggt gcgacaggcc      120
cctggacaag gcttgagtg gatgggaaat atttctccta atagtggtag tgctaactac      180
aatgagaagt tcaagagcag agtcaccatg accagggaca cgtccacgag cacagtctac      240
atggagctga gcagcctgag atctgaggac acggccgtgt attactgtgc gagagagggc      300
ccttacagtt attatccgag tagggagtac tatggctctg acctctgggg gcaagggacc      360
ctagtcacag tctcctcagc ctccaccaag ggcccatcgg tcttccccgct agcgccctgc      420 tccaggagca cctccgagag cacagccgcc ctgggctgcc tggtcaagga ctacttcccc      480
gaaccggtga cggtgtcgtg gaactcaggc gccctgacca gcggcgtgca caccttcccg      540
gctgtcctac agtcctcagg actctactcc ctcagcagcg tggtgaccgt gccctccagc      600
agcttgggca cgaagaccta cacctgcaac gtagatcaca gcccagcaa caccaaggtg       660 gacaagagag ttgagtccaa atatggtccc ccatgcccac cctgcccagc acctgagttc      720 ctgggggac catcagtctt cctgttcccc ccaaaaccca aggacactct catgatctcc       780
cggacccctg aggtcacgtg cgtggtggtg gacgtgagcc aggaagaccc cgaggtccag      840
ttcaactggt acgtggatgg cgtggaggtg cataatgcca agacaaagcc gcggaggag       900 cagttcaaca gcacgtaccg tgtggtcagc gtcctcaccg tcctgcacca ggactggctg      960
aacggcaagg agtacaagtg caaggtctcc aacaaaggcc tcccgtcctc catcgagaaa     1020
accatctcca aagccaaagg gcagccccga gagccacagg tgtacaccct gcccccatcc     1080
caggaggaga tgaccaagaa ccaggtcagc ctgacctgcc tggtcaaagg cttctacccc     1140
agcgacatcg ccgtggagtg ggaaagcaat gggcagccgg agaacaacta caagaccacg     1200
cctcccgtgc tggactccga cggctccttc ttcctctaca gcaggctaac cgtggacaag     1260
agcaggtggc aggaggggaa tgtcttctca tgctccgtga tgcatgaggc tctgcacaac     1320
cactacacac agaagagcct ctccctgtct ctgggt                               1356

<210> SEQ ID NO 6
<211> LENGTH: 642
<212> TYPE: DNA
<213> ORGANISM: Artificial Sequence
<220> FEATURE:
<223> OTHER INFORMATION: synthetic construct

<400> SEQUENCE: 6

-continued

```
gaaattgtgt tgacacagtc tccagccacc ctgtctttgt ctccagggga aagagccacc    60
ctctcctgca gggccagtca agtatcagc aataacctac actggtacca acagaaacct   120
ggccaggctc ccaggctcct catctattat acttcccggt ccgtctctgg catcccagcc   180
aggttcagtg gcagtgggtc tgggacagac ttcactctca ccatcagcag cctagagcct   240
gaagattttg cagtttatta ctgtggacag aataacgagt ggcctgaggt gttcggcgga   300
gggaccaagg tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gc                      642
```

<210> SEQ ID NO 7
<211> LENGTH: 11
<212> TYPE: PRT
<213> ORGANISM: Artificial Sequence
<220> FEATURE:
<223> OTHER INFORMATION: synthetic construct

<400> SEQUENCE: 7

Arg Ala Ser Gln Ser Ile Ser Asn Asn Leu His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: synthetic construct

<400> SEQUENCE: 8

Tyr Thr Ser Arg Ser Val Ser
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic construct

<400> SEQUENCE: 9

Gly Gln Asn Asn Glu Trp Pro Glu Val
1               5

<210> SEQ ID NO 10
<211> LENGTH: 10
<212> TYPE: PRT
<213> ORGANISM: Artificial Sequence
<220> FEATURE:
<223> OTHER INFORMATION: synthetic construct

<400> SEQUENCE: 10

Gly Tyr Glu Phe Thr Ser Tyr Trp Ile His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: synthetic construct

<400> SEQUENCE: 11

Asn Ile Ser Pro Asn Ser Gly Ser Ala Asn Tyr Asn Glu Lys Phe Lys
1               5                   10                  15

Ser

<210> SEQ ID NO 12
<211> LENGTH: 17
<212> TYPE: PRT
<213> ORGANISM: Artificial Sequence
<220> FEATURE:
<223> OTHER INFORMATION: synthetic construct

<400> SEQUENCE: 12

Glu Gly Pro Tyr Ser Tyr Tyr Pro Ser Arg Glu Tyr Tyr Gly Ser Asp
1               5                   10                  15

Leu

<210> SEQ ID NO 13
<211> LENGTH: 452
<212> TYPE: PRT
<213> ORGANISM: Artificial Sequence
<220> FEATURE:
<223> OTHER INFORMATION: synthetic construct

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Glu Phe Thr Ser Tyr
                20                  25                  30

Trp Ile His Trp Val Arg Gln Ala Pro Gly Gln Gly Leu Glu Trp Met
            35                  40                  45

Gly Asn Ile Ser Pro Asn Ser Gly Ser Ala Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Ser Tyr Tyr Pro Ser Arg Gln Tyr Tyr Gly
            100                 105                 110

Ser Asp Leu Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly
    450

<210> SEQ ID NO 14
<211> LENGTH: 126
<212> TYPE: PRT
<213> ORGANISM: Artificial Sequence
<220> FEATURE:
<223> OTHER INFORMATION: synthetic construct

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Glu Phe Thr Ser Tyr
            20                  25                  30

Trp Ile His Trp Val Arg Gln Ala Pro Gly Gln Gly Leu Glu Trp Met
        35                  40                  45

Gly Asn Ile Ser Pro Asn Ser Gly Ser Ala Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Ser Tyr Tyr Pro Ser Arg Gly Tyr Tyr Gly
            100                 105                 110

Ser Asp Leu Trp Gly Gln Gly Thr Leu Val Thr Val Ser Ser
        115                 120                 125

<210> SEQ ID NO 15
```

<211> LENGTH: 214
<212> TYPE: PRT
<213> ORGANISM: Artificial Sequence
<220> FEATURE:
<223> OTHER INFORMATION: synthetic construct

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Thr Ser Arg Ser Val Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Gln Asn Asn Glu Trp Pro Glu
                85                  90                  95

Val Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 107
<212> TYPE: PRT
<213> ORGANISM: Artificial Sequence
<220> FEATURE:
<223> OTHER INFORMATION: synthetic construct

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Thr Ser Arg Ser Val Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Gln Asn Asn Glu Trp Pro Glu
                85                  90                  95

Val Phe Gly Gly Gly Thr Lys Val Glu Ile Lys
            100                 105

<210> SEQ ID NO 17
<211> LENGTH: 1356
<212> TYPE: DNA
<213> ORGANISM: Artificial Sequence
<220> FEATURE:
<223> OTHER INFORMATION: synthetic construct

<400> SEQUENCE: 17

```
caggtgcagc tggtgcagtc tgtgctgaa gtgaagaagc ctggggcctc agtgaaggtg      60
tcctgcaagg catctggcta cgagttcacc agctactgga ttcactgggt gcgacaggcc    120
cctggacaag ggcttgagtg gatgggaaat atttctccta atagtggtag tgctaactac    180
aatgagaagt tcaagagcag agtcaccatg accagggaca cgtccacgag cacagtctac    240
atggagctga gcagcctgag atctgaggac acggccgtgt attactgtgc gagagagggc    300
ccttacagtt attatccgag taggcagtac tatggctctg acctctgggg gcaagggacc    360
ctagtcacag tctcctcagc ctccaccaag ggcccatcgg tcttccccct agcgccctgc    420
tccaggagca cctccgagag cacagccgcc ctgggctgcc tggtcaagga ctacttcccc    480
gaaccggtga cggtgtcgtg gaactcaggc gccctgacca gcggcgtgca ccttcccg      540
gctgtcctac agtcctcagg actctactcc ctcagcagcg tggtgaccgt gccctccagc    600
agcttgggca cgaagaccta cacctgcaac gtagatcaca agcccagcaa caccaaggtg    660
gacaagagag ttgagtccaa atatggtccc ccatgcccac cctgcccagc acctgagttc    720
ctggggggac catcagtctt cctgttcccc ccaaaaccca aggacactct catgatctcc    780
cggacccctg aggtcacgtg cgtggtggtg gacgtgagcc aggaagaccc cgaggtccag    840
ttcaactggt acgtggatgg cgtggaggtg cataatgcca agacaaagcc gcgggaggag    900
cagttcaaca gcacgtaccg tgtggtcagc gtcctcaccg tcctgcacca ggactggctg    960
aacggcaagg agtacaagtg caaggtctcc aacaaaggcc tcccgtcctc catcgagaaa   1020
accatctcca aagccaaagg gcagccccga gagccacagg tgtacaccct gcccccatcc   1080
caggaggaga tgaccaagaa ccaggtcagc ctgacctgcc tggtcaaagg cttctacccc   1140
agcgacatcg ccgtggagtg ggaaagcaat gggcagccgg agaacaacta caagaccacg   1200
cctcccgtgc tggactccga cggctccttc ttcctctaca gcaggctaac cgtggacaag   1260
agcaggtggc aggagggaa tgtcttctca tgctccgtga tgcatgaggc tctgcacaac   1320
cactacacac agaagagcct ctccctgtct ctgggt                             1356
```

<210> SEQ ID NO 18
<211> LENGTH: 642
<212> TYPE: DNA
<213> ORGANISM: Artificial Sequence
<220> FEATURE:
<223> OTHER INFORMATION: synthetic construct

<400> SEQUENCE: 18

```
gaaattgtgt tgacacagtc tccagccacc ctgtctttgt ctccagggga aagagccacc     60
ctctcctgca gggccagtca agtatcagc aataacctac actggtacca acagaaacct    120
ggccaggctc ccaggctcct catctattat acttcccggt ccgtctctgg catcccagcc    180
aggttcagtg gcagtgggtc tgggacagac ttcactctca ccatcagcag cctagagcct    240
gaagattttg cagtttatta ctgtggacag aataacgagt ggcctgaggt gttcggcgga    300
gggaccaagg tggagatcaa acgaactgtg gctgcaccat ctgtcttcat cttccgcca    360
```

```
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gc                      642
```

<210> SEQ ID NO 19
<211> LENGTH: 17
<212> TYPE: PRT
<213> ORGANISM: Artificial Sequence
<220> FEATURE:
<223> OTHER INFORMATION: synthetic construct

<400> SEQUENCE: 19

Glu Gly Pro Tyr Ser Tyr Tyr Pro Ser Arg Gln Tyr Tyr Gly Ser Asp
1               5                   10                  15
Leu

<210> SEQ ID NO 20
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (11)..(11)
<223> OTHER INFORMATION: Xaa position 11 is Glu or Gln

<400> SEQUENCE: 20

Glu Gly Pro Tyr Ser Tyr Tyr Pro Ser Arg Xaa Tyr Tyr Gly Ser Asp
1               5                   10                  15
Leu

<210> SEQ ID NO 21
<211> LENGTH: 73
<212> TYPE: PRT
<213> ORGANISM: Homo sapiens

<400> SEQUENCE: 21

Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
            20                  25                  30

Pro His Cys Ala Gln Thr Glu Val Ile Ala Thr Leu Lys Asn Gly Arg
        35                  40                  45

Lys Ala Cys Leu Asn Pro Ala Ser Pro Ile Val Lys Lys Ile Ile Glu
    50                  55                  60

Lys Met Leu Asn Ser Asp Lys Ser Asn
65                  70

<210> SEQ ID NO 22
<211> LENGTH: 73
<212> TYPE: PRT
<213> ORGANISM: Homo sapiens

<400> SEQUENCE: 22

Ala Pro Leu Ala Thr Glu Leu Arg Cys Gln Cys Leu Gln Thr Leu Gln
1               5                   10                  15

Gly Ile His Leu Lys Asn Ile Gln Ser Val Lys Val Lys Ser Pro Gly
                20                  25                  30

Pro His Cys Ala Gln Thr Glu Val Ile Ala Thr Leu Lys Asn Gly Gln
            35                  40                  45

Lys Ala Cys Leu Asn Pro Ala Ser Pro Met Val Lys Lys Ile Ile Glu
    50                  55                  60

Lys Met Leu Lys Asn Gly Lys Ser Asn
65                  70

<210> SEQ ID NO 23
<211> LENGTH: 73
<212> TYPE: PRT
<213> ORGANISM: Homo sapiens

<400> SEQUENCE: 23

Ala Ser Val Val Thr Glu Leu Arg Cys Gln Cys Leu Gln Thr Leu Gln
1               5                   10                  15

Gly Ile His Leu Lys Asn Ile Gln Ser Val Asn Val Arg Ser Pro Gly
                20                  25                  30

Pro His Cys Ala Gln Thr Glu Val Ile Ala Thr Leu Lys Asn Gly Lys
            35                  40                  45

Lys Ala Cys Leu Asn Pro Ala Ser Pro Met Val Gln Lys Ile Ile Glu
    50                  55                  60

Lys Ile Leu Asn Lys Gly Ser Thr Asn
65                  70

<210> SEQ ID NO 24
<211> LENGTH: 74
<212> TYPE: PRT
<213> ORGANISM: Homo sapiens

<400> SEQUENCE: 24

Ala Ala Val Leu Arg Glu Leu Arg Cys Val Cys Leu Gln Thr Thr Gln
1               5                   10                  15

Gly Val His Pro Lys Met Ile Ser Asn Leu Gln Val Phe Ala Ile Gly
                20                  25                  30

Pro Gln Cys Ser Lys Val Glu Val Ala Ser Leu Lys Asn Gly Lys
            35                  40                  45

Glu Ile Cys Leu Asp Pro Glu Ala Pro Phe Leu Lys Lys Val Ile Gln
    50                  55                  60

Lys Ile Leu Asp Gly Gly Asn Lys Glu Asn
65                  70

<210> SEQ ID NO 25
<211> LENGTH: 75
<212> TYPE: PRT
<213> ORGANISM: Homo sapiens

<400> SEQUENCE: 25

Val Ser Ala Val Leu Thr Glu Leu Arg Cys Thr Cys Leu Arg Val Thr
1               5                   10                  15

Leu Arg Val Asn Pro Lys Thr Ile Gly Lys Leu Gln Val Phe Pro Ala
                20                  25                  30

Gly Pro Gln Cys Ser Lys Val Glu Val Val Ala Ser Leu Lys Asn Gly
            35                  40                  45

Lys Gln Val Cys Leu Asp Pro Glu Ala Pro Phe Leu Lys Lys Val Ile
    50                  55                  60

Gln Lys Ile Leu Asp Ser Gly Asn Lys Lys Asn

-continued

<210> SEQ ID NO 26
<211> LENGTH: 70
<212> TYPE: PRT
<213> ORGANISM: Homo sapiens

<400> SEQUENCE: 26

Ala Glu Leu Arg Cys Met Cys Ile Lys Thr Thr Ser Gly Ile His Pro
1               5                   10                  15

Lys Asn Ile Gln Ser Leu Glu Val Ile Gly Lys Gly Thr His Cys Asn
            20                  25                  30

Gln Val Glu Val Ile Ala Thr Leu Lys Asp Gly Arg Lys Ile Cys Leu
        35                  40                  45

Asp Pro Asp Ala Pro Arg Ile Lys Lys Ile Val Gln Lys Lys Leu Ala
    50                  55                  60

Gly Asp Glu Ser Ala Asp
65                  70

<210> SEQ ID NO 27
<211> LENGTH: 72
<212> TYPE: PRT
<213> ORGANISM: Homo sapiens

<400> SEQUENCE: 27

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70